United States Patent [19]

Haber et al.

[11] Patent Number: 5,366,445
[45] Date of Patent: Nov. 22, 1994

[54] TROCAR WITH ROTATING SAFETY SHIELD

[75] Inventors: Terry M. Haber, Lake Forest; William H. Smedley, Lake Elsinore; Clark B. Foster, Laguna Niguel, all of Calif.

[73] Assignee: Habley Medical Technology Corp., Laguna Hills, Calif.

[21] Appl. No.: 39,910

[22] Filed: Mar. 30, 1993

[51] Int. Cl.⁵ .............................. A61M 5/178
[52] U.S. Cl. .................................. 604/164
[58] Field of Search .............. 604/160, 161, 164, 165, 604/166–169, 272–274; 606/184–185, 171; 128/751–754

[56] References Cited

U.S. PATENT DOCUMENTS

| | | |
|---|---|---|
| 3,994,287 | 11/1976 | Turp et al. . |
| 4,177,814 | 12/1979 | Knepshield et al. . |
| 4,430,081 | 2/1984 | Timmermans ............... 604/256 |
| 4,601,710 | 7/1986 | Moll . |
| 4,610,665 | 9/1986 | Matsumoto et al. ......... 604/167 |
| 4,623,343 | 11/1986 | Thompson . |
| 4,654,030 | 3/1987 | Moll et al. . |
| 4,902,280 | 2/1990 | Lander . |
| 4,931,042 | 6/1990 | Holmes et al. . |
| 5,041,095 | 8/1991 | Littrell ............................ 604/167 |
| 5,053,016 | 10/1991 | Lander . |
| 5,057,084 | 10/1991 | Ensminger et al. .......... 604/167 |
| 5,066,288 | 11/1991 | Deniega et al. . |
| 5,098,405 | 3/1992 | Peterson et al. . |
| 5,127,626 | 7/1992 | Hilal et al. . |
| 5,141,498 | 8/1992 | Christian . |
| 5,167,636 | 12/1992 | Clement . |
| 5,197,955 | 3/1993 | Stephens et al. . |
| 5,226,426 | 7/1993 | Yoon ............................... 128/753 |

FOREIGN PATENT DOCUMENTS

4116648A1 11/1992 Germany .............. A61B 17/34
WO91/17781 11/1991 WIPO .................... A61M 5/178

*Primary Examiner*—John D. Yasko
*Assistant Examiner*—Manuel Mendez
*Attorney, Agent, or Firm*—Townsend & Townsend Khourie & Crew

[57] ABSTRACT

A trocar (2) includes a hollow body (4) defining a path between its proximal and distal ends with an obturator assembly (6) positioned along the path. The distal and (22) of the obturator rod (14) has a cutting element or blade (24). A safety shield (46) is rotably mounted to the blade for automatic movement from a cutting position, with the blade exposed, and a safe position, with the blade shielded, when the blade is at least partially through the tissue layer being pierced. A gas sealing assembly (114) seals the path along the trocar body and includes at least three interleavened elastomeric sealing elements (124) which seal the path when an object, such as an obturator barrel (14), is not positioned along the path.

23 Claims, 7 Drawing Sheets

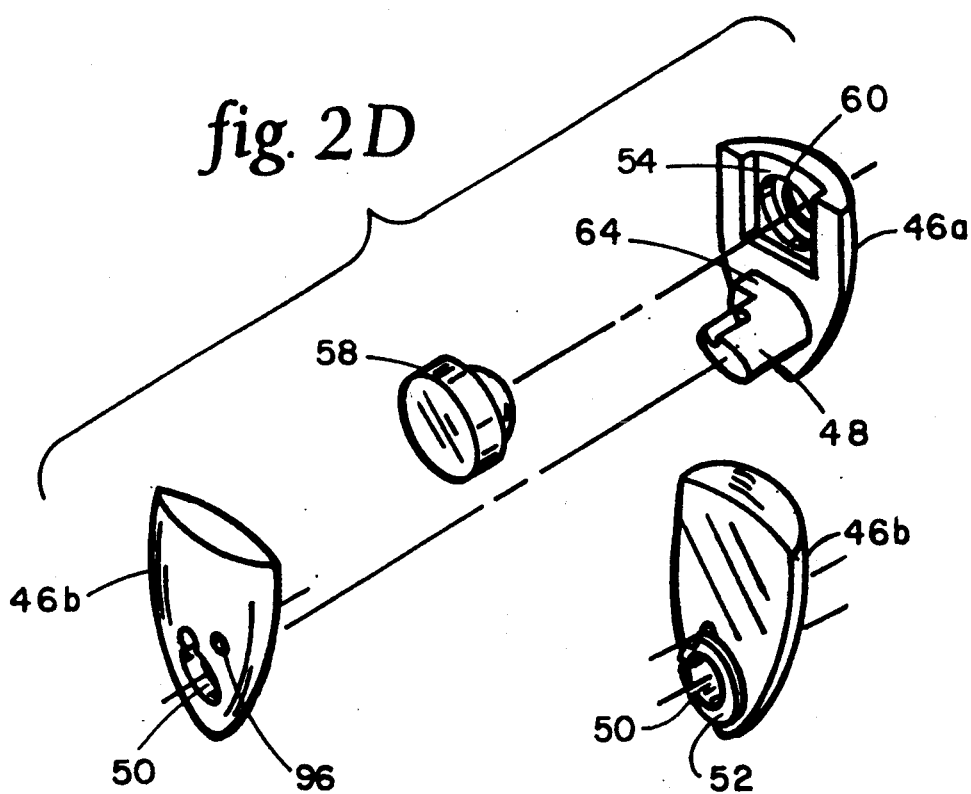
fig. 2D
fig. 2E
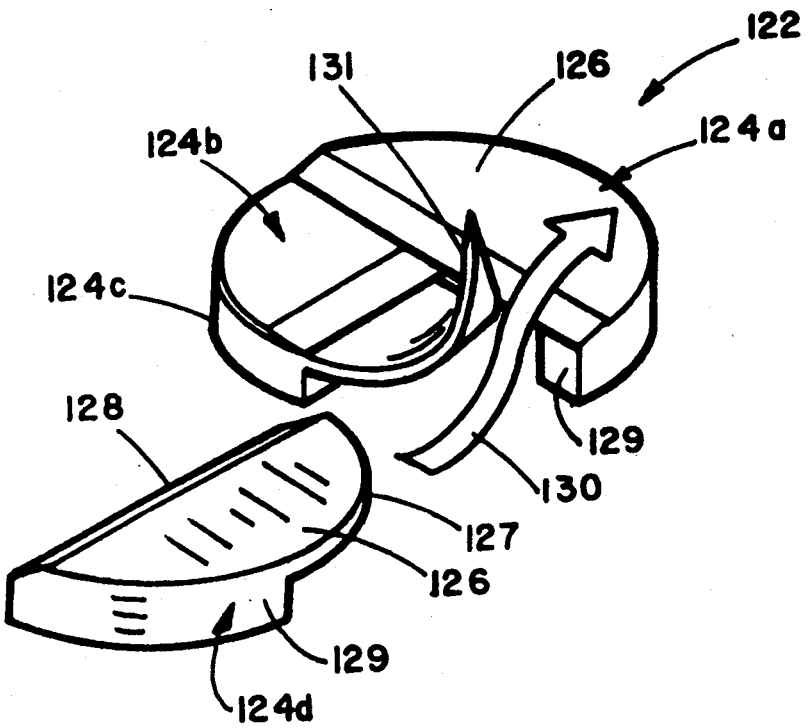
fig. 5

TROCAR WITH ROTATING SAFETY SHIELD

CROSS REFERENCE TO RELATED APPLICATIONS

This is related to U.S. patent application Ser. No. 08/015,170, filed Feb. 9, 1993 for TROCAR; U.S. patent application Ser. No. 08/019,548, filed Feb. 19, 1993 for TROCAR AND SEAL; U.S. patent application Ser. No. 08/031,174 filed Mar. 11, 1993 for TROCAR WITH OVERLAPPING SEAL ELEMENTS; and abandoned U.S. patent application Ser. No. 08/033,315 filed Mar. 15, 1993 for TROCAR WITH IMPROVED OBTURATOR, the disclosures of which are incorporated by reference.

BACKGROUND OF THE INVENTION

Practitioners of medicine or surgery frequently advise a patient to undergo an invasive procedure for either diagnostic or therapeutic reasons. One such invasive procedure involves the use of a trocar which is a sharpened cannula or cylindrical instrument for piercing the wall of a body cavity to minimize traumatization to the tissue through which the endoscopic instrument is passed and to stabilize such endoscopic instrument as well as to provide a seal for insufflation of gasses to expand the operating theater. Thus, the practitioner can gain access to the cavity to withdraw a substance such as a fluid or biopsy specimen, to introduce a gas such as carbon dioxide or an instrument, such as a surgical tool. A laparoscope, a flexible fiberoptic endoscope, is an example of a surgical instrument often introduced through a trocar. The trocar barrel also helps to avoid trauma to the tissue surrounding the opening while inserting and withdrawing a surgical instrument.

Any of the numerous body cavities can be accessible to trocar invasion. Sites for introduction of a trocar include the abdomen and the pelvis. A laparoscope can be introduced through the trocar for visualization, biopsy, and certain surgical procedures. Other body cavities which commonly benefit from endoscopic procedure include the thoracic, cranial, and various joint cavities.

A general technique for introduction of a trocar includes induction of appropriate anesthesia which may be general, local or a combination of both. The area to be pierced by the trocar, such as the skin of the abdomen, is prepped and cleansed conventionally. Typically, the operator makes a nick or a small skin incision with a scalpel blade. The sharpened tip of the conventional trocar is introduced through the nick or incision, and the conventional trocar is pushed downward to and through the fatty tissue. The conventional trocar is further pushed so that its sharpened tip pierces the muscular fascial layer to enter the abdominal cavity.

In the case of laparoscopic surgery (surgery inferior to the diaphragm) a biocompatible gas such as carbon dioxide ($CO_2$) is introduced under pressure into the abdominal cavity to create a space between the muscular fascial layer of the inner abdominal wall and the vital organs posterior to this wall. Such vital organs in the abdomen include the bowel (large and small intestine), the liver, stomach and other structures. Use of $CO_2$ insufflation of the pelvic region tends to protect the bladder and the reproductive organs as well as their associated vascular structures from inadvertent puncture by the sharpened trocar. This is so because of the increased separation between the organs resulting from the expansion of the abdominal cavity due to internal $CO_2$ gas pressure.

A problem attendant to using a sharp tipped trocar in body cavities is the possibility of accidentally piercing or disturbing tissue not intended to be violated. Typically, such tissue is deep to the wall covering the cavity. For example, puncture of the bowel is a complication of trocar use in the abdominal cavity. Complications from inadvertent puncture with the trocar can range from minor to serious. For instance, nicking the uterus with a trocar during a pelvic laparoscopy may be a minor event requiring no therapeutic reaction. Nicking an artery such as the ovarian artery, however, would require immediate surgical repair. Repair may not be possible through a laparoscope but may instead require an open procedure. Similarly, accidental nicking of the intestine could require immediate surgical repair.

Even if repair is undertaken aggressively, complications may ensue. For example, loss of blood from a severed artery could require a transfusion and could result in morbidity or mortality. Similarly, a pierced bowel, although promptly treated, may result in abdominal complications including peritonitis which is an acute inflammatory condition. Other complications can include abdominal infection which, if it goes undetected, can result in abscess formation or subsequent peritonitis. These conditions can be fatal.

The inadvertent puncture of a structure while placing a sharpened trocar can occur in part because the operator is pushing against the abdominal wall inwardly as the trocar is introduced. This action tends to decrease the space between the internal aspect of the abdominal wall and vital structures such as the bowel. In any event, the essential problem is that the trocar is advanced too deeply through and beyond the abdominal facial and cuts into a vital structure accidentally.

One approach to help solve this problem has been the use of auto sheathing. Auto sheathing means that the trocar device includes a means for detecting absence of resistance. When this absence of resistance is encountered, the automatic sheathing device is activated and moves axially to cover or protect the sharpened trocar tip. Typically, this decrease or absence of resistance occurs after puncture of the inner fascial layer and as the trocar tip enters the cavity such as the abdominal cavity which offers minimal or essentially no resistance. Because a vital structure may be very close to the trocar tip shortly after the trocar tip is admitted to the cavity, the time frame for automatic sheathing to act is very narrow.

An additional complication of using the conventional trocar is that the sharpened tip causes a puncturing or incisional pattern in the shape of a Y or other nonlinear pattern. This pattern is not under the control of the operator, but rather is a feature of the device itself. Such a jagged incision tends to heal less rapidly than a simple linear incision. Additionally, in certain tissues such as muscle, a linear incision parallel to the tissue fiber planes permits more rapid healing. In contrast, a cut across the grain of the muscle fiber can prolong the healing process as well as weaken the muscle permanently due to increased formation of granular tissue.

SUMMARY OF THE INVENTION

The present invention is directed to a trocar having an obturator which is slidably housed within a hollow trocar body. The obturator has a pivotal safety shield at the obturator's tip. The safety shield is pivotally mounted to the tip of the obturator for movement between a cutting position, at which the cutting element is exposed, and a safe position, at which the cutting element is covered by the safety shield. This movement occurs automatically with passage of the cutting element at least partly through the tissue layer being cut. In the preferred embodiment the safety shield, which is normally biased from the cutting position to the safe position by spring, is maintained in the cutting position until a release button at the tip of the obturator is depressed. The release button is positioned so that the cut tissue depresses the release button to permit the safety shield to pivot, under the influence of the spring, from the cutting position to the safe position. However, the pivot point of the safety shield when in the cutting position is forward or distal of the center of the safety shield. This helps to ensure the safety shield remains in or close to the cutting position during the initial cutting of the tissue layer since the cut tissue keeps the safety shield from pivoting to the safe position. Only after the tip of the obturator is at least substantially through the tissue layer can the safety shield pivot around its own axis to the safe position. This occurs automatically and very quickly after the tip of the obturator has passed fully or partially through the tissue layer to help prevent inadvertent injury to structures internal of the tissue layer being cut.

An advantage of the invention relates to the type of incision made by the invention. A simple, linear incision may permit the wound to heal much more quickly than the multilobed puncture wound created by a conventional obturator. Also, the surgeon can orient the direction of the cut created by the present invention so that the cut is made parallel to tissue fiber planes to promote rapid healing. An indicating line denoting orientation of the plane of the cutting blade permits rotational alignment of the cutting blade and plane to be made parallel to muscle fibers direction for minimum trauma and minimum healing time. This is not possible when using conventional trocars.

A seal is used for sealing the path along the body of the trocar. The seal seals the path both when the obturator or any surgical device is within the trocar body and once the obturator/surgical device has been removed from the trocar body. The seal includes at least three, and preferably four, overlapping elastomeric sealing elements stacked on top of one another in an interleavened manner so that a portion of each said sealing element overlaps an adjacent sealing element and is overlapped by another adjacent sealing element. Each of the sealing elements have a distal edge extending across the path. The distal edges are arranged at angles to one another. The distal edges cross at a common location so to seal the path when an object is not positioned along the path. The sealing elements are configured to permit an obturator or other surgical instrument to pass therethrough and to seal the path by sealingly engaging the exterior of the obturator/surgical instrument.

The region of the hollow interior of the trocar body distal of the sealing elements is preferably selectively coupled to a pressurized gas source and to atmosphere. This allows the physician to pressurize or vent the body cavity through the trocar. It is preferred that the material for the sealing elements be chosen and the elements be configured to accommodate a range of diameters from, for example, 5 mm to 11.4 mm, that is a range in diameters from x to at least 2x. Also, when configuring the object-engaging surfaces and choosing the material, care must be taken to minimize the amount of force required to past the instrument through the gas seal.

Other features and advantages of the invention will appear from the following description in which the preferred embodiment has been set forth in detail in conjunction with the accompanying drawings.

BRIEF DESCRIPTION OF THE DRAWINGS

FIG. 2D is an enlarged exploded isometric view of the shield of FIG. 2;

FIG. 2E is an isometric view of one-half of the shield of FIG. 2D showing the pulley;

FIG. 5 is an isometric view of the set of four elastomeric sealing elements of FIG. 2 illustrating their interleavened assembly.

DESCRIPTION OF THE PREFERRED EMBODIMENT

Figure 1:
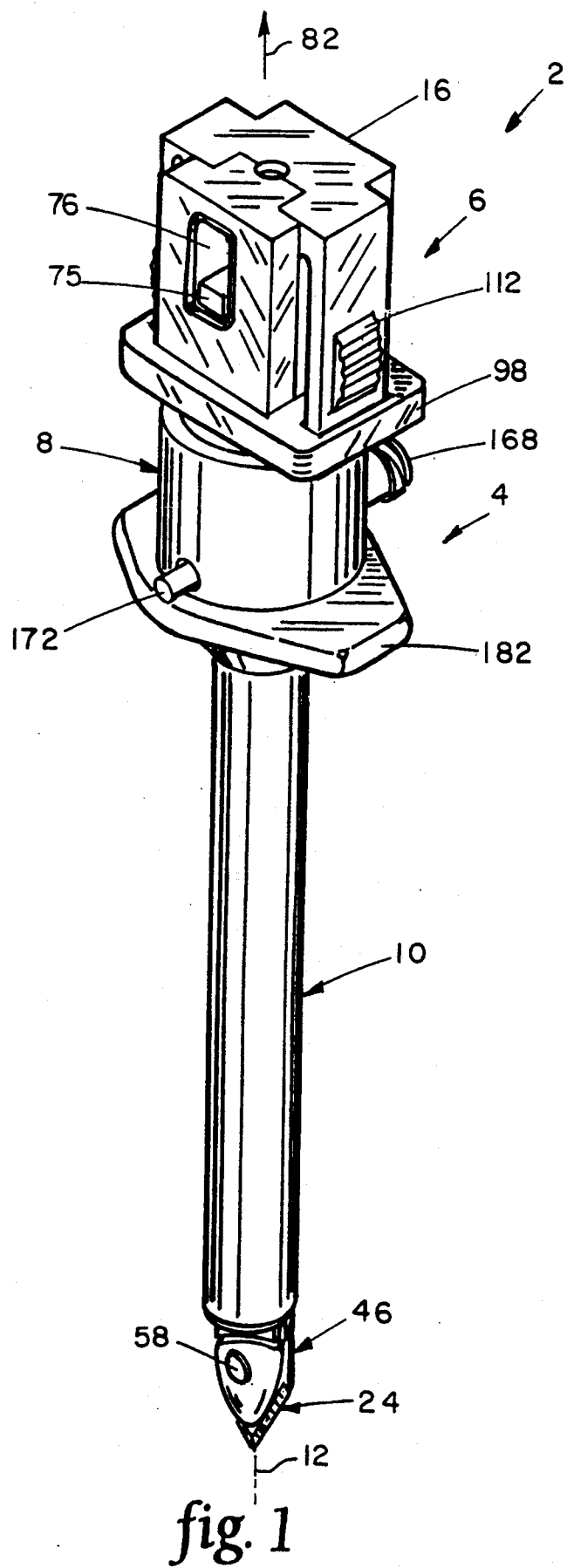
FIG. 1 is an overall isometric view of a trocar made according to the invention.
Figure 2:
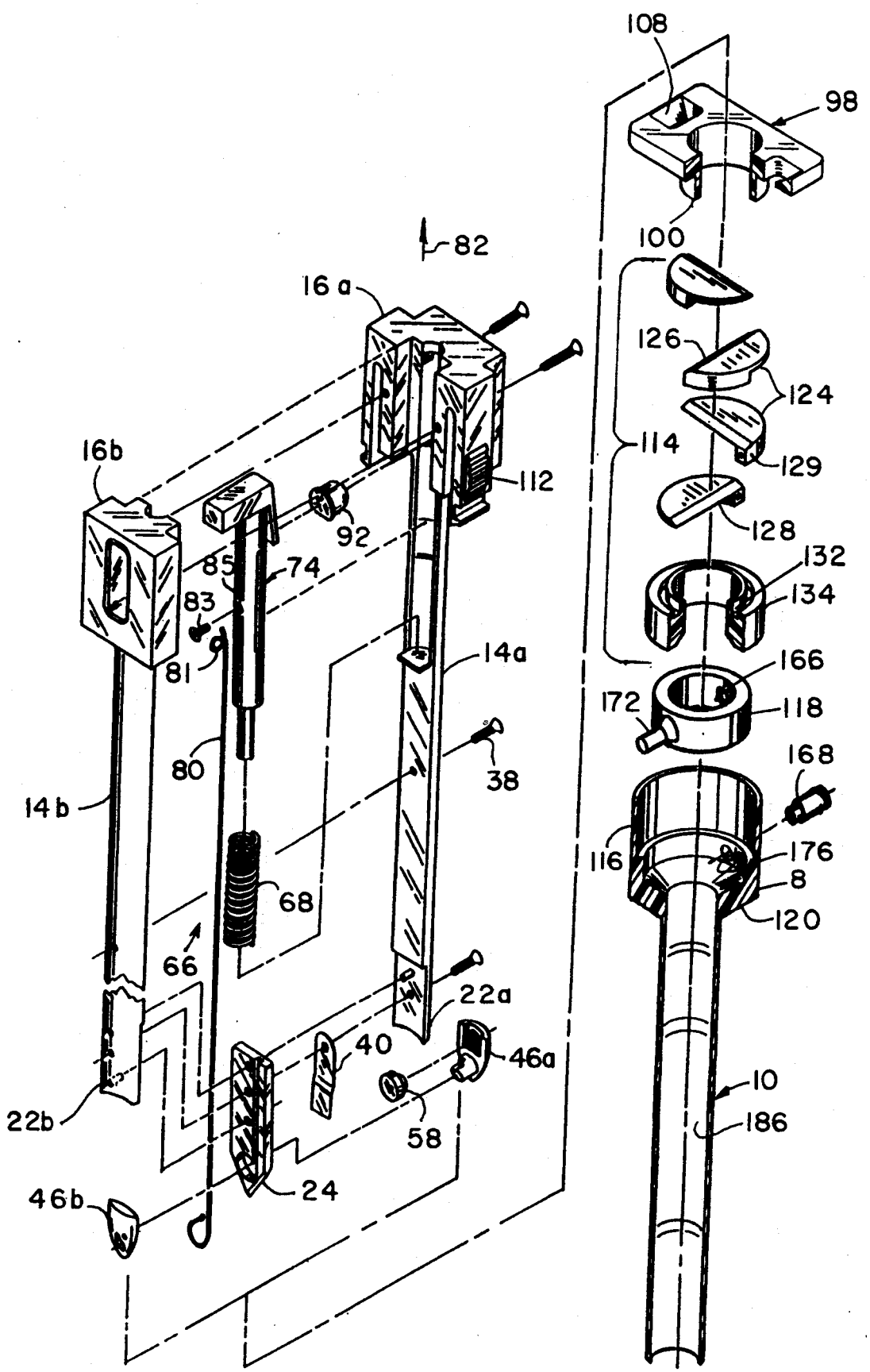
FIG. 2 is an exploded isometric view of the trocar of FIG. 1.

FIGS. 1–2E illustrate a trocar 2 including a trocar body 4 to and within which an obturator assembly 6 is slidably mounted. Trocar body 4 is hollow and includes a trocar base 8 to which a tubular trocar barrel 10 is secured, such as with an adhesive. Trocar barrel 10 defines a central axis 12 of trocar 2 and is sized to guide the obturator barrel 14 therein.

Figure 2A:
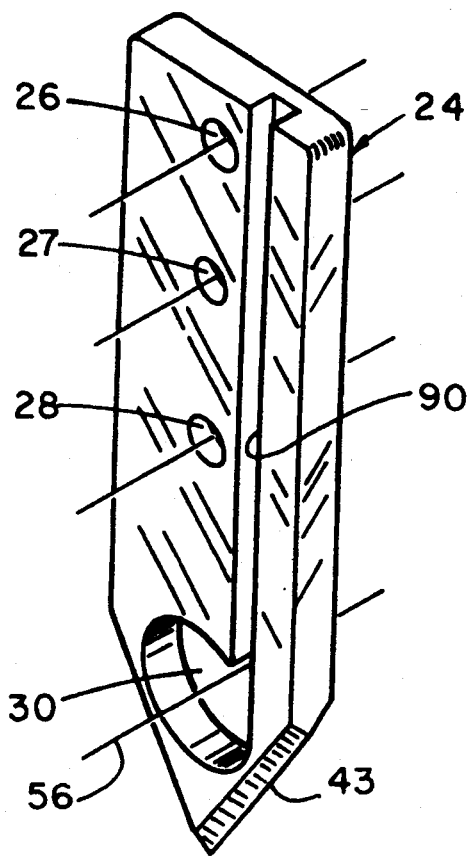
FIGS. 2A and 2B are enlarged isometric views of either side of the blade of FIG. 2.
Figure 2B:
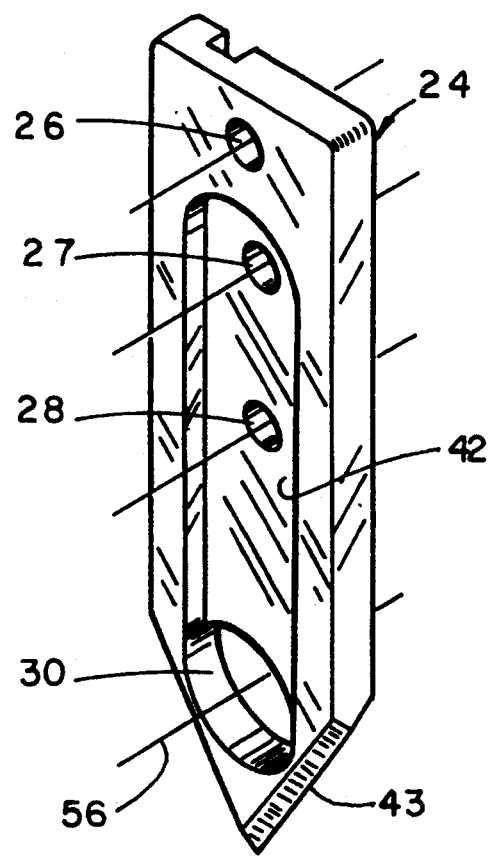
Figure 2C:
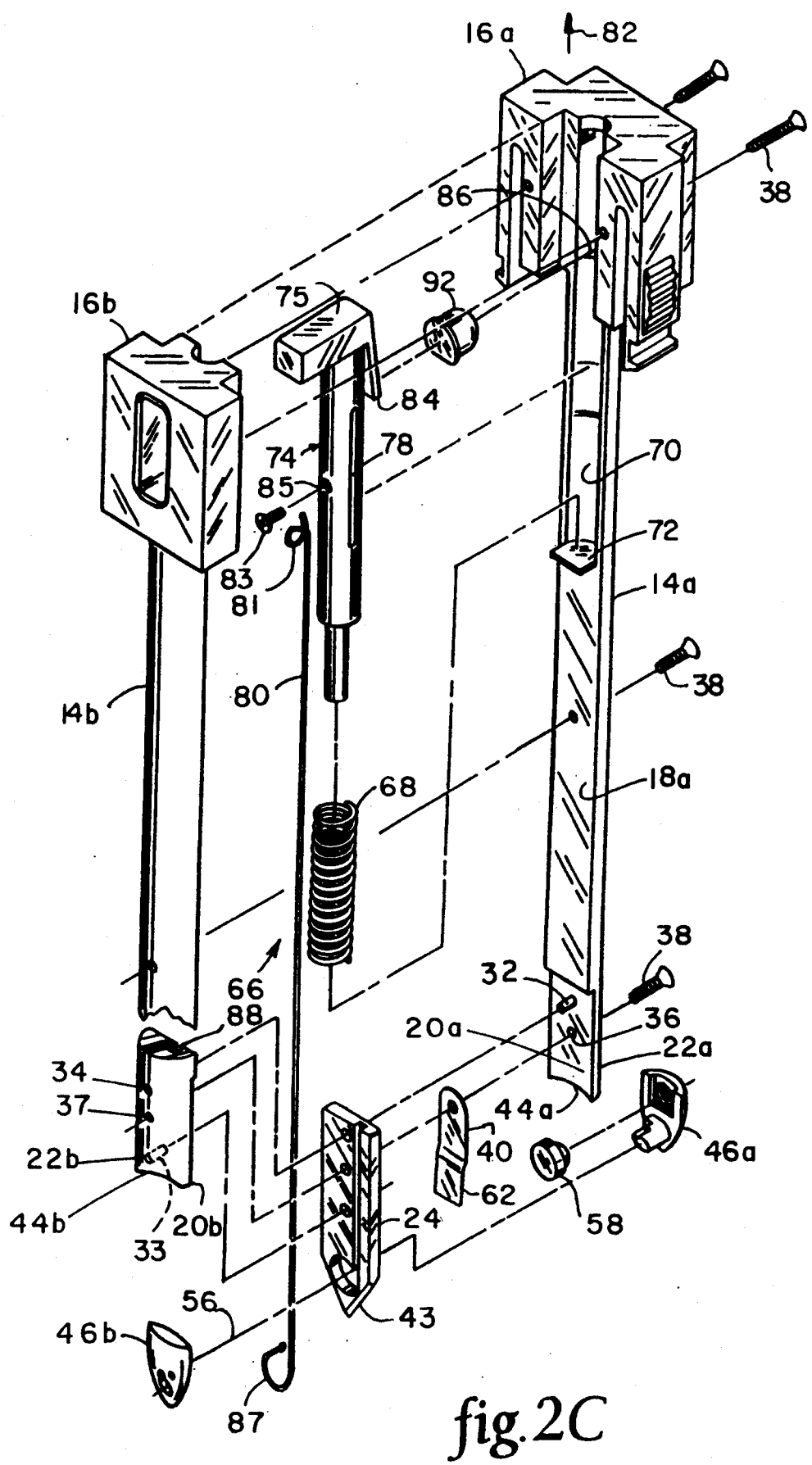
FIG. 2C is an enlarged exploded isometric view of the obturator assembly of FIG. 2.

Obturator assembly 6 includes obturator body 16 from which an obturator rod 14 extends. Obturator rod and body are both two piece members including obturator rod halves 14a, 14b and body halves 16a, 16b. The abutting faces 18a, 18b of obturator rod halves 14a, 14b have cut outs or recesses 20a, 20b at the distal ends 22a, 22b of obturator rod halves 14a, 14b. Obturator blade 24, shown best in FIGS. 2A and 2B, is securely mounted within recesses 20a, 20b at distal end 22 of obturator rod 14. Blade 24 includes three small holes 26, 27, 28 and one large hole 30 formed therethrough. Holes 26, 28 align with pins 32, 33 extending from rod halves 14a, 14b at distal ends 22a, 22b. Pin 32 is sized sufficiently long to pass completely through hole 26 and into a hole 34 formed in distal end 22b of obturator rod half 14b. Pin 33 is sized so that it passes into hole 28 but does not pass through hole 28. Distal ends 22a, 22b also include holes 36, 37 situated between pins 32, 33 and aligned with hole 27 in blade 24. Rod halves 14a, 14b and body halves 16a, 16b have other holes within which screws 38 are mounted to secure halves 14a, 14b, 16a, 16b together. The screw 38 passing through hole 27 in blade 24 also secures a generally flat spring 40 within a cut out 42 formed on one side of blade 24.

Figure 3:
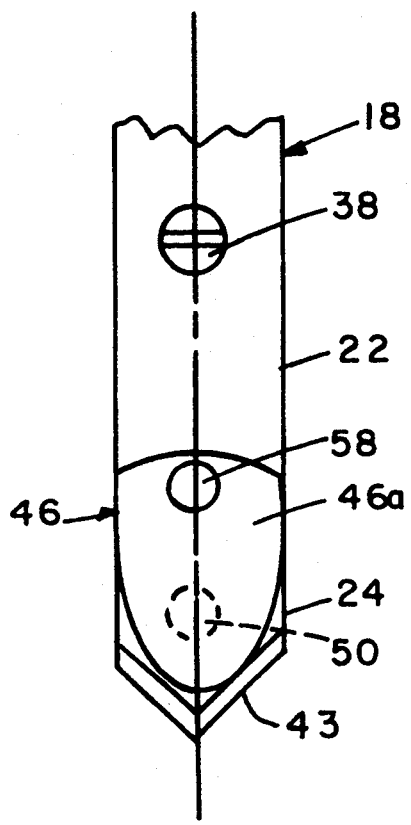
FIGS. 3 and 4 are enlarged views of the distal ends of the obturator assembly of FIG. 1 shown in the cutting and the safe positions.

The outer surfaces of safety shield 46 and obturator rod 14 adjacent arcuate ends 44a, 44b of rod halves 14a, 14*b* are aligned to provide a smooth transition between the two when safety shield 46 is in the cutting position of FIGS. 1 and 3. This prevents the interface from catching or snagging on the tissue layer being cut.

Blade 24 has a generally V-shaped cutting edge 43 which extends beyond the arcuate ends 44*a*, 44*b* of rod halves 14*a*, 14*b*. Large hole 30 is positioned entirely beyond arcuate ends 44*a*, 44*b*. A safety shield 46 is rotatably mounted to obturator blade 24 through large hole 30. Safety shield 46 includes shield halves 46*a*, 46*b*. Half 46*a* has an axle 48 extending through a complementary hole 50 and half 46*b*; halves 46*a*, 46*b* are keyed together so they rotate as a unit.

Half 46*b* has an integral pulley 52 concentric with hole 50 and positioned to fit within large hole 30 on the side of blade 24 opposite cutout 42, that is the side shown in FIG. 2A. Normally, flat spring 40 is biased outwardly away from cutout 42 and into a pocket 54 found in shield half 46*a*. Since the width of flat spring 40 is about the same as the width of pocket 54, this keeps safety shield 46 from rotating about the axis 56 of hole 30 when the end 62 of spring 40 is within pocket 54. To permit this rotary motion, a button 58, carried within a stepped hole 60 formed in shield half 46*a* is pushed radially inwardly so that the outer end 62 of flat spring 40 is removed from pocket 54 and back into slot 42. Doing so permits safety shield 46 to rotate about axis 56. This rotary motion is, however, limited by the engagement of a tab 64, extending radially from axle 48 and positioned within large hole 30, with outer end 62 of flat spring 40; this engagement of tab 64 with outer end 62 limits the rotary motion of safety shield 46 to about 180° between the cutting position of FIG. 3 and the safe position of FIG. 4.

Safety shield 46 is driven along its 180° arc by a spring driver assembly 66. Spring driver assembly 66 includes a compression coil spring 68 mounted between rod halves 14*a*, 14*b* and housed within a generally cylindrical housing 70 formed between the two. Spring 68 rests against a base 72 at the distal end of housing 70 and an indicator shuttle 74 at the proximal end of housing 70. Indicator shuttle 74 has an L-shaped indicator head 75 which is positioned opposite an indicator view window 76 in body half 16*b*. Indictor shuttle 74 has an axially extending slot 78 through which the proximal end 81 of a tension cable 80 passes.

Figure 4:
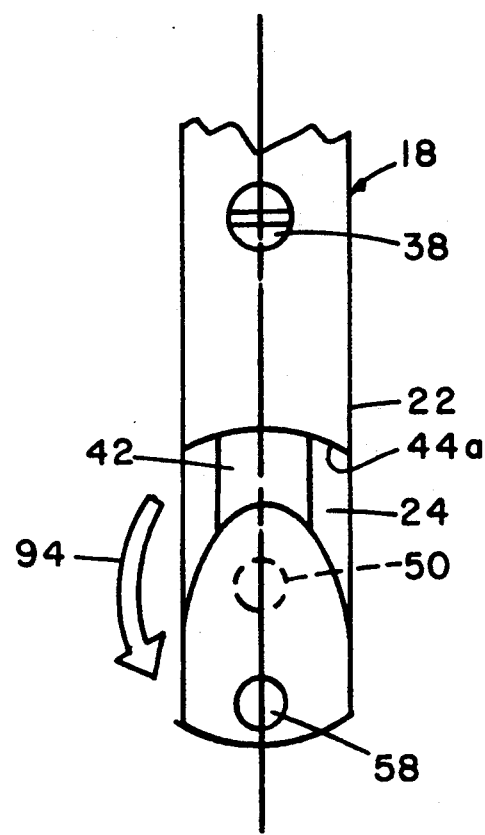

Cable 80 passes from shuttle 74, along one side of base 72, along a slot 88 in rod half 14*b* and through a slot 90 in blade 24. The distal end 87 of tension cable 80 is secured to pulley 52 using the same key used to key safety shield halves 46*a*, 46*b* together Spring 68 being under compression tends to drive indictor shuttle 74 in a proximal direction 82. This tends to move safety shield 46 from the cutting position of FIG. 3 to the safe position of FIG. 4. This movement, as discussed above, is prevented by the engagement of end 62 of flat spring 40 within pocket 54 until button 58 is depressed. When in the cutting position of FIG. 3, head 75 of indicator shuttle 74 is in a distal position within window 76. See FIG. 1. Movement of safety shield 46 from the cutting position of FIG. 3 to the safe position of FIG. 4 is indicated to the user by movement of head 75 from a distal position within window 76 to a proximal position within the window. Thus, the user has an accurate indication of whether safety shield 46 is in the cutting or safe position even if distal end 22 is not visible.

Indicator shuttle 74 also includes an outwardly extending stop 84 which engages a shelf 86 formed in cylindrical housing 70 when safety shield 46 is in the safe position. Stop 84, when engaged with shelf 86, prevents distal movement of indicator shuttle 74 and thus keeps safety shield 46 in the safe position. To reset obturator assembly 6, the user pushes on a button 92, mounted in a hole formed in body half 16*a*, which presses against stop 84 to disengage stop 84 from shelf 86. The user can now rotate safety shield back to the cutting position of FIG. 3, that is in the direction opposite arrow 94 of FIG. 4 against the force of spring 68. When returned to the cutting position of FIG. 3, end 62 of spring 40 enters pocket 54 formed in shield half 46*a* to keep safety shield 46 in the cutting position. This movement of safety shield 46 is preferably accomplished using a pointed tool inserted into a hole 96 in shield half 46*b* to help prevent injury from blade 24.

As is shown in FIG. 3, more than half, and preferably more than 2/3, of safety shield 46 is located in proximal direction 82 of shield axis 56. This configuration helps to ensure that safety shield remains in essentially the cutting position of FIGS. 1 and 3 until blade 24 has at least substantially, and typically completely, cut the tissue layer being breached.

Trocar body 4, see FIGS. 3 and 4, includes a locking plate 98 having a hollow cylindrical boss 100 sized to fit within the tubular proximal end 102 of trocar base 8. Locking plate 98 has a pair of tapered latching surfaces 108 positioned above and radially outwardly of proximal end 102 of base 8. Latching surfaces 108 are sized to accommodate the distal ends of resilient docking hooks 112 at the distal end of obturator body 58. Placing the distal end of obturator body 16 against locking plate 98, shown in FIG. 1, causes docking hooks 112 to engage latching surfaces 108, to be biased inwardly and then to snap outwardly to latch beneath surfaces 108 thus securing obturator assembly 6 to trocar body 4.

Trocar body 4 includes a sealing assembly 114 mounted within the proximal, enlarged cylindrical portion 116 of trocar base 8 and an elastomeric vent ring 118 positioned adjacent an inwardly and distally tapering region 120 at the distal end of trocar base 8. Sealing assembly 114 includes a seal 122 made from four elastomeric sealing elements 126. Each sealing element 126 is generally semicircular in shape having a main body portion 126 with a semicircular peripheral edge 127 and a tapered or feathered distal edge 128. Each elastomeric sealing element includes a thickened region 129 extending over approximately half of peripheral edge 127. FIG. 5 illustrates the interleavened arrangement of elastomeric sealing elements 124 in which element 124*a* is positioned so that about one-half of main body portion 126 overlies main body portion 126 of element 124*b* which likewise overlies main body portion 126 of element 124*c*. As indicated by arrow 130 of FIG. 5A, element 124*d* is inserted under the flexible outer portion 131 of element 124*c* with the outer portion 131 of main body portion 126 of element 124*d* placed on top of main body portion 126 of element 124*a*. It should be noted that this interleavened arrangement in which each elastomeric sealing element 124 lies on top of another element 124 and is overlain by a third element 124 provides an effective seal both when obturator rod 14 is within trocar body 4 and when obturator rod 14 is removed from trocar body 4. The use of tapered distal edges 128 helps ensure the proper sealing effectiveness at the center of proximal seal 122 where edges 128 meet. Elastomeric sealing elements 124 are preferably made from 50

Durometer silicone rubber for its toughness and good sealing qualities.

Figure 6A:
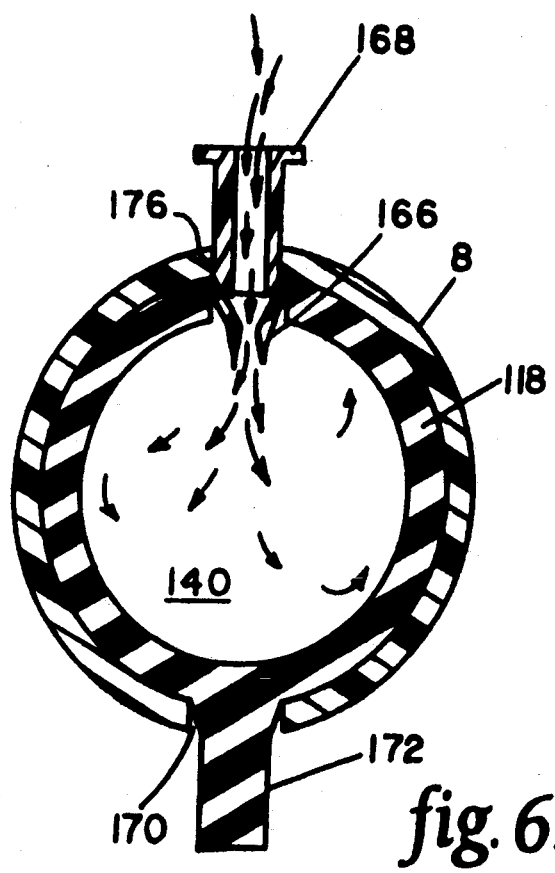
FIGS. 6A and 6B are plan cross-sectional views of the trocar body and elastomeric vent ring of FIG. 4 shown with pressurized fluid passing into the interior of the trocar body in FIG. 6A and the opening of a vent path to the ambient environment in FIG. 6B.
Figure 6B:
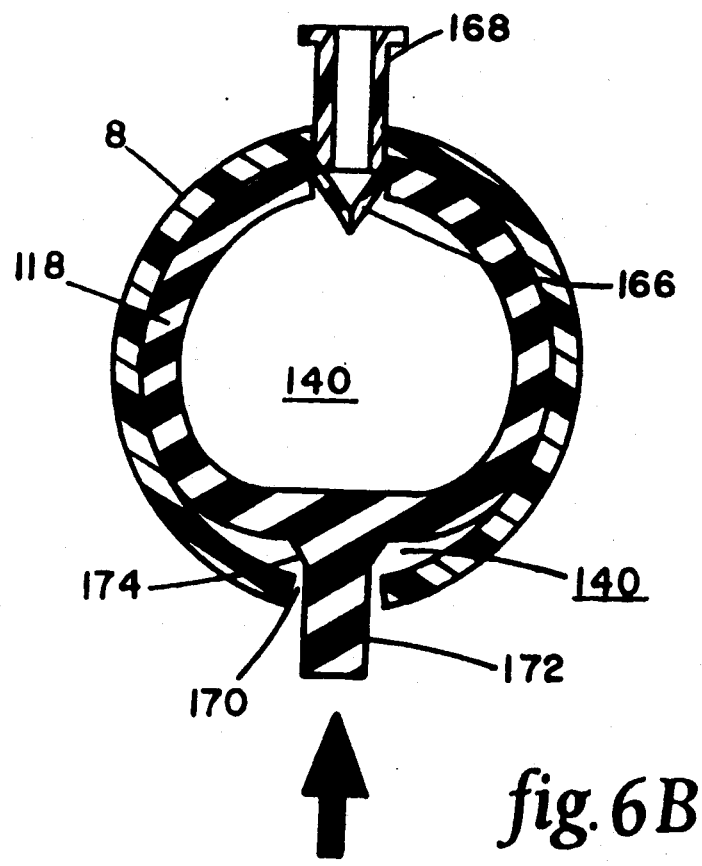

A spacer ring 134 is mounted between seal 122 and vent ring 118, see FIGS. 2, 6A and 6B. Thickened regions 129 are housed within an upper annular groove 132 formed in spacing 134. Vent ring 118 is made from an elastomeric material, such as 50 Durometer silicone rubber, and includes an integral conical check valve 166 which is aligned with a radially extending Luer lock fitting 168 mounted within a hole 176 in base 8. A remote pressure source (not shown) is connected to fitting 168. Check valve 166 allows fluid to pass into interior 140 of body 8, as suggested in FIG. 6A, but not the reverse, as suggested in FIG. 6B. Base 8 has a radially extending bore 170 through which a radial extension 172 of ring 118 passes. The enlarged base 174 of extension 172 is biased against bore 170 with sufficient force to normally seal bore 170. To vent interior 140, the user simply presses on extension 172 which deflects ring 118 radially inwardly as shown in FIG. 6B. This provides a vent path from interior 140 to the ambient environment through bore 170. Accordingly, with the invention separate medical devices need not be used to either pressurize or vent the body cavity accessed by trocar 2.

The final element of trocar body 4 is a finger ledge 182. Finger ledge 182 is secured to the outside of base 8, such through an adhesive or using a friction fit.

The present invention is made from conventional biocompatible materials. For example, blade 24, springs 40, 68, cable 80 plus the various screws are preferably made from stainless steel. Sealing elements 124 and vent ring 118 are preferably made of a suitable elastomeric materials, as discussed above. The remaining parts can be made of polycarbonate or other appropriate materials. It is particularly important that trocar base 8 and trocar barrel 10 be made of biocompatible materials.

In use, the physician first makes a small incision with a scalpel at the point of entry. The tapered tip of obturator assembly 6 is then pressed through the slit in the patient's skin, through the fatty tissue layer until the tip reaches the muscular fascial layer. As this is occurring, the cut tissue depresses button 58 to release end 62 of spring 40 from pocket 54. Once blade 24 is through the muscular fascial layer, the force exerted on safety shield 46 by the tissue is insufficient to keep safety shield 46 from rotating about 180° to the safe position of FIG. 4. Obturator assembly 6 is then removed from trocar body 4 by pressing on docking hooks 112 and lifting the obturator assembly in proximal direction 87. As the tip of obturator assembly 6 passes sealing elements 124, the sealing elements return to their sealing positions of FIG. 5 to prevent escape of fluid pressure through trocar 2. An endoscopic surgical instrument, such as an endoscope, can then be inserted through trocar body, past sealing assembly 114, through the interior 186 of trocar barrel 10 and into the body cavity. The surgical instrument is surrounded by sealing elements 124 to help prevent the loss of pressurization within the body cavity. The body cavity can be pressurized by simply mounting a pressurized line to fitting 168 and supplying pressurized fluid, typically $CO_2$, into interior 140, through interior 186 and into the body cavity. The pressure in the body cavity can be reduced by pressing on extension 172 which deflects vent ring 118 and permits fluid flow through bore 170 and to the ambient environment. To reset obturator assembly 6 to the cutting position of FIGS. 1 and 3, button 92 is depressed and safety shield 46 is rotated in the direction opposite arrow 94 until in the cutting position of FIG. 3 at which end 62 of spring 40 enters pocket 54.

Modifications and variations can be made to the disclosed embodiment without departing from the subject of the invention as defined in the following claims. For example, sealing assembly 114 could be used with other medical devices designed for minimally invasive surgical procedures. Also, seal 122 could be used with other sealing elements as well. Four sealing elements 124 need not be used, three or more could be used. Edges 127 need not be straight and elements 124 need not be all the same size. Blade 24 could be other than straight and could have three cutting edges.

What is claimed is:

1. A trocar, used to provide an opening through a tissue layer, comprising:
   a trocar body having a hollow interior; and
   an obturator assembly having proximal and distal ends, the distal end of the obturator assembly sized to pass through the hollow interior of the trocar body, the obturator assembly including:
      a cutting element at the distal end, the cutting element having a tip;
      a safety shield pivotally mounted to the distal end and adjacent the cutting element, the safety shield being pivotal between a cutting position, with the cutting element exposed to the tissue layer, and a safe position, with the safety shield shielding the cutting element; and
      means for automatically rotating the safety shield from the cutting position to the safe position upon passage of at least the tip of the cutting element through the tissue layer.

2. The trocar of claim 1 wherein the cutting element includes a flat blade.

3. The trocar of claim 1 wherein the obturator assembly has an axis and the safety shield rotates about a shield axis oriented generally perpendicular to the axis of the obturator assembly.

4. The trocar of claim 3 wherein the flat blade includes a V-shaped cutting edge.

5. The trocar of claim 4 wherein the shield axis is located adjacent a proximal portion of the V-shaped cutting edge.

6. The trocar of claim 3 wherein the safety shield is configured so that when the safety shield is in the cutting position, at least ½ of the safety shield is proximal of the shield axis.

7. The trocar of claim 3 wherein the safety shield is configured so that when the safety shield is in the cutting position at least 2/3 of the safety shield is proximal of the shield axis.

8. The trocar of claim 1 wherein the obturator assembly includes an obturator barrel having an outer surface and the safety shield includes an outside surface.

9. The trocar of claim 8 wherein the safety shield has an arcuate proximal end surface and the trocar body has a complementary distal surface opposite the arcuate proximal end surface when the safety shield is in the cutting position with the outer surface and the outside surface providing a smooth transition therebetween.

10. The trocar of claim 1 wherein the safety shield rotating means includes a shield driver biasing the safety shield in a rotary direction from the cutting position to the safe position.

11. The trocar of claim 10 wherein the safety shield includes a pulley and the shield driver includes a drive spring and a tension cable, the tension cable coupling the drive spring and the pulley.

12. The trocar of claim 10 wherein the shield driver includes an indicator providing a user with an indication of whether the safety shield is in the cutting position or the safe position.

13. The trocar of claim 10 wherein the safety shield rotating means includes a safety shield release element at the distal end of the obturator assembly positioned to be engaged by the tissue layer after the cutting element has at least partially cut the tissue layer.

14. The trocar of claim 13 wherein the safety shield release element is operable between a safety shield engaged condition, at which the safety shield is maintainable in the cutting position against the shield driver, and a safety shield released position, at which the safety shield is released to be rotatable by the shield driver from the cutting position to the safe position, the safety shield release element being operable to the safety shield released position when said safety shield release element has been engaged by said tissue.

15. The trocar of claim 13 wherein the release element is positioned a distance proximally of the cutting element.

16. The trocar of claim 1 further comprising:
a seal mounted within the body and fluidly sealing the hollow interior with and without the obturator assembly directed into the hollow interior, the seal including at least three overlapping elastomeric sealing elements stacked on top of one another in an interleavened manner so that a portion of each said sealing element overlaps an adjacent sealing element and is overlapped by another adjacent sealing element, each of said sealing elements having a distal edge extending across the hollow interior, the distal edges being arranged at angles to one another and crossing at a common location so to seal the path when an object is not positioned along the path, said sealing elements configured to permit the object to pass therethrough.

17. The medical device of claim 16 including four said overlapping sealing elements arranged at 90° intervals so that first and second of said distal edges are parallel and third and fourth of said distal edges are perpendicular to said first and second distal edges.

18. The trocar of claim 1 further comprising:
a resilient vent ring, having an interior surface and an exterior surface, mounted within the hollow interior;
a passageway formed from the interior surface, through the body and to a port exterior of the body;
a check valve positioned along the passageway to permit fluid flow through the port, along the passageway and into the hollow interior but to prevent fluid flow from the hollow interior, through the passageway and through the port; and
a vent ring deflector extending from the vent ring through a vent in the body to a user-accessible position exterior of the body, the vent ring deflector movable from a normally sealed position, at which the vent ring and vent ring deflector seal the vent to prevent fluid flow from the hollow interior and through the vent, to a vent position, at which the vent ring is deflected inwardly into the hollow interior to permit fluid flow from the hollow interior, through the vent and into a region exterior of the body.

19. An improved obturator assembly of the type, used to provide an opening through a tissue layer, having proximal and distal ends and a cutting element at the distal end, the improvement comprising:
a safety shield pivotally mounted to the distal end and adjacent the cutting element, the safety shield being pivotal between a cutting position, with the cutting element exposed to the tissue layer, and a safe position, with the safety shield shielding the cutting element; and
means for automatically rotating the safety shield from the cutting position to the safe position upon passage of at least a portion of the safety shield through the tissue layer.

20. A trocar, used to provide an opening through a tissue layer, comprising:
a trocar body having a hollow interior; and
an obturator assembly having proximal and distal ends and defining an obturator axis therebetween, the distal end of the obturator assembly sized to pass through the hollow interior of the trocar body, the obturator assembly including:
a flat bladed cutting element fixed to a the distal end;
a safety shield pivotally mounted to the distal end and adjacent the cutting element, the safety shield being pivotal about a shield axis perpendicular to the obturator axis between a cutting position, with the cutting element exposed to the tissue layer, and a safe position, with the safety shield shielding the tissue layer from cutting element;
the safety shield being configured so that when the safety shield is in the cutting position at least 2/3 of the safety shield is proximal of the shield axis;
means for automatically rotating the safety shield from the cutting position to the safe position upon passage of at least a portion of the cutting element through the tissue layer;
the safety shield rotating means including a shield driver biasing the safety shield in a rotary direction from the cutting position to the safe position, the safety shield including a pulley and the shield driver including a drive spring and a tension cable, the tension cable coupling the drive spring and the pulley; and
the safety shield rotating means including a safety shield release button at the distal end of the obturator assembly positioned to be engaged by the tissue layer after the cutting element has at least partially cut the tissue layer, the safety shield release button being movable between a safety shield engaged condition, at which the safety shield is maintainable in the cutting position against the shield driver, and a safety shield released position, at which the safety shield is released to be rotatable by the shield driver from the cutting position to the safe position, the safety shield release button being movable to the safety shield released position when said safety shield release button has been depressed by said tissue.

21. The trocar of claim 20 further comprising:
a seal mounted within the body and fluidly sealing the hollow interior with and without the obturator assembly directed into the hollow interior, the seal including at least three overlapping elastomeric sealing elements stacked on top of one another in an interleavened manner so that a portion of each said sealing element overlaps an adjacent sealing element and is overlapped by another adjacent sealing element, each of said sealing elements having a distal edge extending across the hollow interior, the distal edges being arranged at angles to one another and crossing at a common location so to seal the path when an object is not positioned along the path, said sealing elements configured to permit the object to pass therethrough.

22. The medical device of claim 21 including four said overlapping sealing elements arranged at 90° intervals so that first and second of said distal edges are parallel and third and fourth of said distal edges are perpendicular to said first and second distal edges.

23. The trocar of claim 20 further comprising:
a resilient vent ring, having an interior surface and an exterior surface, mounted within the hollow interior;
a passageway formed from the interior surface, through the body and to a port exterior of the body;
a check valve positioned along the passageway to permit fluid flow through the port, along the passageway and into the hollow interior but to prevent fluid flow from the hollow interior, through the passageway and through the port; and
a vent ring deflector extending from the vent ring through a vent in the body to a user-accessible position exterior of the body, the vent ring deflector movable from a normally sealed position, at which the vent ring and vent ring deflector seal the vent to prevent fluid flow from the hollow interior and through the vent, to a vent position, at which the vent ring is deflected inwardly into the hollow interior to permit fluid flow from the hollow interior, through the vent and into a region exterior of the body.

* * * * *